US00PP37309P3

(12) United States Plant Patent
Langella

(10) Patent No.: US PP37,309 P3
(45) Date of Patent: Mar. 3, 2026

(54) ***CAMPANULA* PLANT NAMED 'KLECN23085'**

(50) Latin Name: ***Campanula portenschlagiana* Schult. x *Campanula poscharskyana* Degen**
Varietal Denomination: KLECN23085

(71) Applicant: KLEMM + SOHN GMBH & CO. KG, Stuttgart (DE)

(72) Inventor: Raffaele Langella, Rome (IT)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 18/778,114

(22) Filed: Jul. 19, 2024

(65) Prior Publication Data

US 2025/0120329 P1 Apr. 10, 2025

(30) Foreign Application Priority Data

Oct. 5, 2023 (QZ) ..... PBR 2023/2100

(51) Int. Cl.
*A01H 5/02* (2018.01)
*A01H 6/26* (2018.01)

(52) U.S. Cl.
USPC ..... Plt./414
CPC ..... *A01H 6/264* (2018.05)

(58) Field of Classification Search
USPC ..... Plt./414
CPC ..... A01H 5/02
See application file for complete search history.

*Primary Examiner* — Kent L Bell
(74) *Attorney, Agent, or Firm* — Weatherly IP Solutions, LLC; James M. Weatherly

(57) ABSTRACT

A new *Campanula* plant particularly distinguished by a semi-upright mounding habit, very high and dense branching with compact behavior, early flowering habit; and Campanulate-shaped flowers with violet colored petals, is disclosed.

1 Drawing Sheet

Genus and species: *Campanula portenschlagiana* Schult. x *Campanula poscharskyana* Degen.
Variety denomination: 'KLECN23085'.

CROSS-REFERENCE TO RELATED APPLICATION

This patent application claims the benefit of priority from Community Plant Breeders Rights Application No. 2023/2100 as filed on Oct. 5, 2023, the contents of which are incorporated herein by reference for all it teaches and discloses.

BACKGROUND OF THE NEW PLANT

The present invention comprises a new and distinct variety of *Campanula*, botanically known as *Campanula portenschlagiana* Schult. x *Campanula poscharskyana* Degen, and hereinafter referred to by the variety name 'KLECN23085'. 'KLECN23085' originated from an open cross-pollination in June 2019 in Stuttgart, Germany between an unnamed female *Campanula* variety (unpatented) and an unnamed male *Campanula* variety (unpatented).

The seeds from the cross were collected and sown in Stuttgart, Germany in the summer of 2020 and the plants were grown for evaluation. An individual plant designated 'KLECN23085' was selected in the autumn 2020 in Stuttgart, Germany. In the autumn 2020 'KLECN23085' was first vegetatively propagated by vegetative terminal cuttings in Stuttgart, Germany. 'KLECN23085' was found to reproduce true to type in successive generations of asexual propagation via vegetative cuttings.

SUMMARY

The following are the most outstanding and distinguishing characteristics of this new variety when grown under normal horticultural practices in Stuttgart, Germany.

1. Semi-upright mounding habit, dense canopy of plant;
2. Very highly branching with compact habit;
3. Early flowering habit; and
4. Campanulate-shaped flowers with violet colored petals.

DESCRIPTION OF THE PHOTOGRAPH

This new *Campanula* plant is illustrated by the accompanying photograph which shows a close-up of the foliage, buds, and mature flower. The photograph is of a 13-week-old plant grown indoors in Stuttgart, Germany in April 2023. The colors shown are as true as can be reasonably obtained by conventional photographic procedures.

DESCRIPTION OF THE NEW VARIETY

The following detailed descriptions set forth the distinctive characteristics of 'KLECN23085'. The data which define these characteristics were collected in Stuttgart Germany in summer 2023 on 13 to 15 week old plants. References are to The R.H.S. Colour Chart of The Royal Horticultural Society of London (R.H.S.), 5$^{th}$ edition (2007).

Classification:

*Family*.—Campanulaceae.
*Botanical*.—*Campanula portenschlagiana* Schult. x *Campanula poscharskyana* Degen.
*Common*.—*Campanula*.
*Designation*.—'KLECN23085'.

Parentage:

*Female parent*.—Unnamed selection of *Campanula portenschlagiana*, not patented.

*Male parent*.—Unnamed selection of *Campanula poscharskyana*, not patented.

Plant:

*Asexual propagation*.—By cuttings.

*Form*.—Globular, mounding, densely branching.

*Habit*.—Semi-upright habit, dense and bushy.

*Vigor*.—Compact, short height.

*Roots*.—Fine, well branched; white to pale yellow in color.

*Color*.—RHS NN155 to RHS 19C.

*Height* (*from soil line to top of foliage*).—8.0 cm to 8.5 cm.

*Spread*.—20.0 cm.

Propagation:

*Type cuttings*.—Unrooted cuttings; Terminal vegetative cuttings, from stock plants maintained at short days.

*Time to produce a rooted cutting*.—About 26 to 28 days at 19° C. to 21° C.

*Pest and disease resistance*.—Under commercial production conditions, plants of the new *Campanula* have not been noted to be resistant to pathogens or pests common to *Campanula*.

Stems:

*Average number of stems*.—50 to 60.

*Stem color*.—RHS 144D.

*Pubescence*.—Present.

*Pubescence color*.—RHS 144D.

*Stem description*.—Strong stem branched up to 7 to 8 sub-branches each able to carry flowers.

*Stem diameter*.—0.2 mm.

*Stem length*.—10.0 cm to 12.0 cm. From soil line to first node: 0.5 cm to 0.8 cm. Total length: 12.0 cm.

*Internode length*.—0.5 cm to 1.0 cm.

*Anthocyanin*.—Present.

*Color*.—RHS 145A.

Leaves:

*Description*.—Simple.

*Arrangement*.—Alternate.

*Shape*.—Cordate.

*Apex*.—Acuminate.

*Base*.—Truncate to cordate.

*Margin*.—Broadly dentate, serrate to biserrate.

*Length*.—1.5 cm.

*Width*.—1.3 cm.

*Texture*.—Upper surface: Moderately rugose, rough. Lower surface: Moderately rugose, rough.

*Pubescence*.—Upper surface: Slightly pubescent. Lower surface: Moderately pubescent.

*Color*.—Young leaf expanding: Upper surface: RHS N137D. Lower surface: RHS 147B. Mature leaves: Upper surface: RHS N137A. Lower surface: RHS 147B.

*Veins*.—Description: Palmate. Vein color: Upper surface: RHS 144A. Lower surface: RHS 144B.

Petiole:

*Description*.—All leaves are petiolate.

*Shape*.—Semi-cylindrical with the flat part (slightly grooved on the sides) facing upwards.

*Texture*.—Moderately pubescent.

*Margin*.—Entire.

*Color*.—Upper surface: RHS 137B. Lower surface: RHS 144B.

Inflorescence:

*Flowering type*.—Single star-shaped campanulate.

*Flowering season*.—May to October under natural light conditions.

*Duration of flowers*.—3 to 9 days depending on temperature.

*Description*.—At apex; attitude outright to slightly upright.

*Height*.—1.5 cm to 1.8 cm.

*Width*.—2.2 cm to 2.5 cm.

Flower:

*Description*.—Single star-shaped campanulate flowers arranged in panicles.

*Length*.—1.5 cm to 1.8 cm (top to the base of corolla).

*Width*.—2.2 cm to 2.5 cm.

*Fragrance*.—Not detected.

*Number of flowers*.—Per stem: 35 to 40. Per plant: 1000 to 2500 (buds to open flowers).

Flower buds:

*Shape*.—Ovate, elliptic.

*Apex*.—Acuminate to rounded.

*Base*.—Rounded.

*Length*.—0.6 mm to 1.6 mm.

*Width*.—0.2 mm to 0.4 mm.

*Flower bud color*.—RHS 144A a slight tinge of RHS 85A with RHS N88A on upper parts of opening corolla.

Petals:

*Description*.—Lanceolate petals fused at the base.

*Shape*.—Lanceolate.

*Apex*.—Acute.

*Base*.—Fused with other petals.

*Margin*.—Entire.

*Length*.—2.0 cm to 2.2 cm.

*Width*.—0.5 cm to 0.6 cm.

*Texture*.—Smooth internally and externally where rare hairiness externally especially along the main vein and in the distal part of the petal.

*Pubescence*.—Very poor, on main vein especially along the main vein and in the distal part of the petal.

*Petal color*.—Upper surface: RHS N88B. Lower surface: RHS N87A.

Corolla:

*Description*.—Five sepals in a single whorl, fused at the base, star shaped.

*Length*.—1.5 cm to 1.8 cm.

*Width*.—2.2 cm to 2.5 cm.

*Shape*.—Campanulate-star shaped.

Sepal:

*Number*.—5.

*Shape*.—Narrow lanceolate, grouped in number of five in a single whorl, star-shaped calix fused at the base.

*Apex*.—Acute.

*Base*.—Fused.

*Margin*.—Entire.

*Length*.—0.6 cm to 0.9 cm.

*Width*.—0.1 cm to 0.2 cm.

*Texture*.—Upper surface: Moderately pubescent. Lower surface: Moderately pubescent.

*Color*.—Upper surface: RHS N138A. Lower surface: RHS N138A.

*Calyx*.—Length: 0.8 cm. Width: 0.7 cm.

*Peduncle*.—Number per plant: 500. Description: Semi-cylindrical stem adaptation sustaining robust panicle. Shape: Semi-cylindrical straight shape with upright tendency. Texture: Fine pubescence. Attitude: Straight, upright. Strength: Robust. Length: 8.5 cm to 11.5 cm. Width: 0.2 cm to 0.22 cm. Average number of nodes: 11 to 13. Internode spacing: 0.7 cm to 1.4 cm. Branching description: Numerous lateral branches that emerge from each node, leading to a dense, bushy, and freely branching structure well distributed forming ball, mounding shaped plants. Color: RHS 145A to RHS 145B.

*Pedicel*.—Shape: Semi-cylindrical. Length: 0.7 cm to 1.2 cm. Width: 0.1 cm. Texture: Fine pubescence. Color: RHS 144A.

Androecium:

*Number*.—5.

*Filament*.—Length: 0.2 cm. Width: 0.15 cm. Color: RHS 4D.

*Anther*.—Description: Enlarged at base. Length: 0.6 cm to 0.7 cm. Width: 0.05 cm to 0.15 cm base. Color: RHS NN155B to RHS NN155C.

*Pollen*.—Amount: Scarce. Color: RHS 20A.

*Gynoecium*.—Length: 1.0 cm to 1.2 cm.

*Style*.—Shape: cylindrical. Length: 0.9 cm. Width: 0.05 cm. Color: RHS 92A.

*Stigma*.—Description: Tripartite. Length: 0.1 cm. Width: 0.25 cm. Color: RHS 91B.

*Ovary*.—Length: 0.15 cm. Width: 0.25 cm. Color: RHS 145A.

Seed:

*Shape*.—Elliptic.

*Length*.—0.06 cm to 0.08 cm.

*Width*.—0.03 cm to 0.04 cm.

*Texture*.—Shiny, slightly rugose.

*Color*.—RHS175A.

COMPARISON WITH PARENTAL LINES AND KNOWN VARIETY

'KLECN23085' is a distinct variety of *Campanula* and is distinguished from its parents as described in Table 1.

TABLE 1

Comparison with Parental Lines

| Characteristic | 'KLECN23085' | Female Parent | Male Parent |
|---|---|---|---|
| Earliness | 8.5 weeks (with 14 hrs of day light) | 1 week earlier than 'KLECN23085' | 2 weeks later than 'KLECN23085' |
| Flower color | Violet | Lighter than 'KLECN23085' | Darker than 'KLECN23085' |
| Growth habit | Compact, Rounded-mounding | Flat growing | Bushy growing |
| Leaf color | Grey green | Normal green | Normal green |

'KLECN23085' is most similar to the commercial *Campanula* variety Campala® 'Nina' (not patented). Differences between the varieties are described in Table 2.

TABLE 2

Comparison with Similar Variety

| Characteristic | 'KLECN23085' | 'Nina' |
|---|---|---|
| Corolla colour | Darker colour than 'Nina' | Lighter colour than 'KLECN23085' |
| Shape of plant | More rounded than 'Nina' | More upright than 'KLECN23085' |
| Earliness | 10 days later than 'Nina' | 10 days earlier than 'KLECN23085' |

I claim:

1. A new and distinct cultivar of *Campanula* plant named 'KLECN23085' as illustrated and described herein.

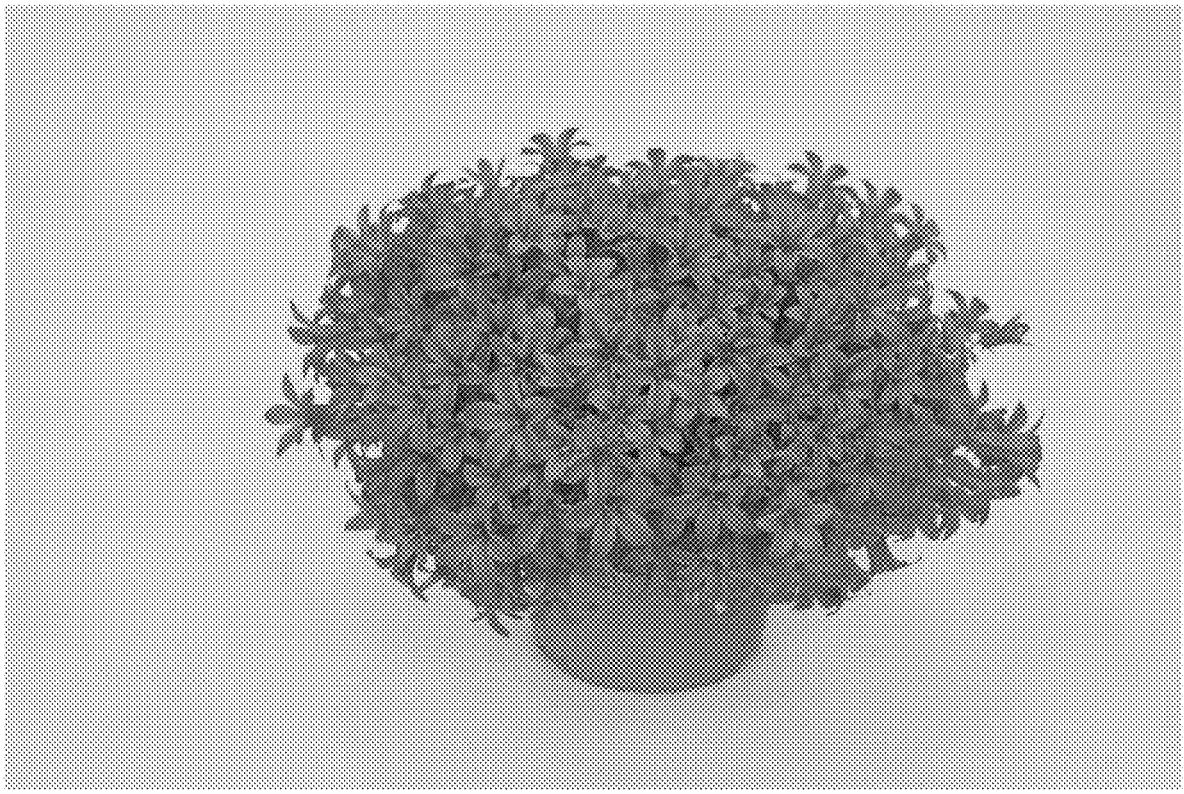

* * * * *